United States Patent [19]
Kelm et al.

[11] Patent Number: 5,651,983
[45] Date of Patent: Jul. 29, 1997

[54] BISACODYL DOSAGE FORM FOR COLONIC DELIVERY

[75] Inventors: Gary Robert Kelm, Cincinnati; Gary Lee Manring, Hamilton; Paula Denise Davis, Cincinnati; Douglas Joseph Dobrozsi, Loveland; Kenneth Gary Mandel, Fairfield; David Lee McCauley-Meyers, Middletown, all of Ohio

[73] Assignee: The Procter & Gamble Company, Cincinnati, Ohio

[21] Appl. No.: 442,915

[22] Filed: May 17, 1995

Related U.S. Application Data

[63] Continuation-in-part of Ser. No. 558,338, Nov. 15, 1995, which is a continuation of Ser. No. 279,361, Jul. 22, 1994, abandoned, which is a continuation of Ser. No. 23,412, Feb. 26, 1993.

[51] Int. Cl.$^6$ ............... A61K 9/20; A61K 9/22; A61K 31/715; A61K 47/40
[52] U.S. Cl. ............... 424/452; 424/464; 424/465; 424/468; 514/58; 514/777; 514/778
[58] Field of Search ............... 424/452, 464, 424/465, 468; 514/58, 777, 778

[56] References Cited

U.S. PATENT DOCUMENTS

| | | | |
|---|---|---|---|
| 2,764,590 | 9/1956 | Kottler et al. | |
| 3,431,338 | 3/1969 | Munzel | 424/21 |
| 4,432,966 | 2/1984 | Zeitoun et al. | 424/21 |
| 4,816,259 | 3/1989 | Matthews et al. | 424/463 |
| 4,822,629 | 4/1989 | Pong | 424/480 |
| 4,834,985 | 5/1989 | Elger et al. | 424/488 |
| 4,910,021 | 3/1990 | Davis et al. | 424/456 |
| 4,952,402 | 8/1990 | Sparks et al. | 424/419 |
| 5,068,110 | 11/1991 | Fawzi et al. | 424/461 |
| 5,171,580 | 12/1992 | Iamartino et al. | 424/490 |
| 5,283,064 | 2/1994 | Suzuki et al. | 424/451 |
| 5,330,759 | 7/1994 | Pagay et al. | 424/462 |

FOREIGN PATENT DOCUMENTS

| | | |
|---|---|---|
| 839625 | 7/1976 | Belgium . |
| 0225189 | 11/1986 | European Pat. Off. . |
| 0313845 | 9/1988 | European Pat. Off. . |
| 53-133625 | 11/1978 | Japan . |
| 57-099521 | 6/1982 | Japan . |
| 63-20409 | 6/1982 | Japan . |
| 59-139317A | 8/1984 | Japan . |
| 59-193816 | 11/1984 | Japan . |
| 61-221117 | 10/1986 | Japan . |
| 63-258815A | 10/1988 | Japan . |
| 01117826A | 5/1989 | Japan . |
| 2151921 | 7/1985 | United Kingdom . |
| WO83/00435 | 2/1983 | WIPO . |

OTHER PUBLICATIONS

Schmidt, P.C., "The MiniWiD-Coater: II. Comparison of Acid Resistance of Enteric-Coated Bisacodyl Pellets Coated With Different Polymers," Drug Development & Industrial Pharmacy, vol. 18, No. 18 (1992), pp. 1969–1979.

Luce, G.T., "Disintegration of tablets enteric coated with cellulose acetate phthalate," Pharm. Tech., vol. 2 (Oct. 1978), pp. 51–55.

Spitael, J., et al. "Enteric Coating using cellulose acetate phthalate", Manuf. Chem., vol. 57, No. 8 (Aug. 1986), pp. 35, 37.

Kane, Y. et al. "Technological evaluation of three enteric coating polymers. Part I. With an insoluble drug," Drug Dev. Ind. Pharm., vol. 19, No. 16 (1993), pp. 2011–2020.

Luce, G.T., "Disintegration of tablets enteric coated with CAP (cellulose acetate phthalate)," Manuf. Chem. Aerosol News, vol. 49, No. 50 (1978), pp. 50, 52, 67.

Preston, D.M., "Pelvic Motility and Response to Intraluminal Bisacodyl in Slow-Transit Constipation," Digestive Diseases & Sciences, vol. 30, No. 4 (1985), pp. 289–294.

Kamm, M.A. et al., "Dynamic scanning defines a colonic defect in severe idiopathic constipation," Gut, vol. 29 (1988), pp. 1085–1092.

Jauch, R. et al., "Bis–(p–hydroxyphenyl)–pyridyl–2–methane: The Common Laxative Principle of Bisacodyl and Sodium Picosulfate," Arzneim.–Forsch. (Drug Res.), vol. 25, No. 11 (1975), pp. 1796–1800.

Roth, W., "Translation of Pharmacokinetics and Laxative Effect of Bisacodyl After Administration of Various Dosage Forms," Arzneim.–Forsch./Drug Res., vol. 38(1), No. 4 (1988), pp. 570–574.

Leng-Peschlow, E., "Effects of Sennosides A +B and Bisacodyl on Rat Large Intestine," Pharmacology, vol. 38 (1989), pp. 310–318.

Rasmussen, S., "Intestinal Absorption of Quinine from Enteric Coated Tablets," Acta Pharmacol. et Toxicol vol. 24 (1966) pp. 331–345.

*Primary Examiner*—Carlos Azpuru
*Attorney, Agent, or Firm*—Betty J. Zea

[57] ABSTRACT

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of rapidly dissolving bisacodyl incorporated into or coated on the surface of a dosage form selected from the group consisting of a spherical substrate, an elliptical substrate, a hard capsule, or a compressed tablet, with a maximum diameter of about 3 mm to about 10 mm; and b. an enteric polymer coating material;

wherein the dosage form has a smooth surface free from edges or sharp curves; the elliptical substrate and the hard capsule have a ratio of the long to short diameters of no greater than about 1.5; the rapidly dissolving bisacodyl is released at a point near the inlet to, or within the colon; the enteric polymer coating material begins to dissolve in an aqueous media at a pH between about 5 to about 6.3; and the enteric polymer coating material has a coating thickness of at least about 250 µm.

29 Claims, No Drawings

BISACODYL DOSAGE FORM FOR COLONIC DELIVERY

This is a continuation-in-part of application Ser. No. 08/558,338, filed Nov. 15, 1995, which is a continuation of application Ser. No. 08/279,361, filed on Jul. 22, 1994, now abandoned, which is a continuation of application Ser. No. 08/023,412, filed Feb. 26, 1993.

TECHNICAL FIELD

The present invention relates to novel spherical unit dosage forms containing bisacodyl for colonic delivery to provide laxation in the colon.

BACKGROUND OF THE INVENTION

Bisacodyl, 4,4'-(2-pyridylmethylene)bisphenoldiacetate, is disclosed in the Merck Index, 11 th ed. (1989), S. Budavari, ed., No. 1253, p. 193. Bisacodyl is an inactive prodrug that is hydrolyzed by intestinal brush border enzymes and colonic bacteria to desacetyl bisacodyl which is the active species. (R. Jauch, R. Hankwitz, K. Beschke, & H. Pelzer, "Bis-(p-hydroxyphenyl)-pyridyl-2-methane: The Common Laxative Principle of Bisacodyl and Sodium Picosulfate", Arzneim.-Forsch./Drug Res. 25 (11), 1796–1800, 1975). Contact of desacetyl bisacodyl with the mucosa of the colon stimulates sensory nerve endings to produce increased propulsive peristaltic contractions of the colon which accelerate movement of contents through the colon. Both bisacodyl and desacetyl bisacodyl are poorly water soluble with absorption reported from both the small intestine and the colon. Absorption from the small intestine may be greater than from the colon.

Delivery of suspensions or solutions of bisacodyl to the colon is known to result in laxation. (M. A. Kamm, J. E. Lennard-Jones, D. G. Thompson, R. Sobnack, N. W. Garvie, N. Granowska, "Dynamic Scanning Defines a Colonic Defect in Severe Idiopathic Constipation", Gut, Vol 29, pp 1085–1092, 1988; D. M. Preston, J. E. Lennard-Jones, "Pelvic Motility and Response to Intraluminal Bisacodyl in Slow-Transit Constipation", Digestive Diseases and Sciences, Vol 30, No 4, pp 289–294, 1985; E. Leng-Peschlow, "Effect of Sennosides A+B and Bisacodyl on Rat Large Intestine", Pharmacology, Vol 38, pp 310–318, 1988).

A dosage form that truely delivers a concentrated form of bisacodyl, rapidly, to the colon, with minimum absorption occurring in the small intestine, would be desirable for several reasons. Since desacetyl bisacodyl acts upon contact with the lumenal mucosa of the colon, its laxative effect is dependent upon generation of sufficient levels of the drug in the lumen of the colon. However, it has been determined that secondary diarrhea and/or repeat bowel movements associated with peroral administration of bisacodyl are at least partially due to the fact that absorbed desacetyl bisacodyl is partially excreted in the bile as the glucuronide conjugate which can be subsequently cleaved by colonic bacteria releasing desacetyl bisacodyl. Therefore, it is desirable to minimize absorption of desacetyl bisacodyl from the small intestine and colon while achieving therapeutically effective levels of the drug in the lumen of the colon. Lower doses of bisacodyl can be used if bisacodyl is delivered in an undiluted, rapidly dissolving form, to its site of activity in the colon. Low doses will provide laxation efficacy with minimal side effects such as repeat bowel movements, cramping, and secondary diarrhea.

Release of bisacodyl in the colon as a preferred mode of delivery of the drug in order to minimize systemic absorption of bisacodyl is disclosed in W. Roth, K. Beschke, "Pharmacokinetics and Laxative Effect of Bisacodyl after Administration of Various Dosage Forms", Arzneim.-Forsch./Drug Res., Vol. 38(I), No. 4 (1988), pp. 570–574.

Commercially-available bisacodyl compositions are typically coated with a low level of an enteric polymer or combination of polymers. An example of such a commercially available product is Dulcolax® (Boehringer Ingelheim Pharmaceuticals, Ridgefield, Conn.). (See also, enteric coated bisacodyl tablets indicated for the relief of constipation in the Physician's Desk Reference for Non Prescription Drugs, 13th ed. (1992), p. 550.) Dulcolax® is typically coated with a low level of cellulose acetate phthalate, and each tablet has about 5 mg of bisacodyl. The recommended dose is from 1 to 3 tablets (from 5 to 15 mg of bisacodyl). Another example is Colac® (Procter & Gamble Pharmaceuticals) which is coated with a low level of a 50/50 mixture of Eudragit® S and Eudragit® L, with the same recommended dosing as Ducolox®. These bisacodyl formulations are formulated in such a way that they are not rapidly dissolving once the bisacodyl reaches the colon. In addition the level of coating is much less than the amount required by the present invention.

Colonic delivery dosage forms are known in the art. For example, U.S. Pat. No. 5,171,580, issued Dec. 15, 1992, Boehringer Ingelheim Italia, teaches a preparation for delivery in the large intestine and especially the colon, comprising an active containing core coated with three protection layers of coatings having different solubilities. The inner layer is Eudragit® S, with a coating thickness of about 40–120 microns, the intermediate coating layer is a swellable polymer with a coating thickness of about 40–120 microns, and the outer layer is cellulose acetate phthalate, hydroxypropylmethyl cellulose phthalate, polyvinyl acetate phthalate, hydroxyethyl cellulose phthalate, cellulose acetate tetrahydrophthalate, or Eudragit® L.

U.S. Pat. No. 4,910,021, issued on Mar. 20, 1990, Scherer Corp., teaches a targeted delivery system wherein the composition comprises a hard or soft gelatin capsule containing an active ingredient such as insulin and an absorption promoter, which is coated with a film forming composition being sufficiently soluble at a pH above 7 as to be capable of permitting the erosion or dissolution of said capsule. The film forming composition is preferably a mixture of Eudragit® L, Eudragit® RS, and Eudragit® S at specific ratios to provide solubility above a pH of 7. Coating levels above what is known in the art are not disclosed.

U.S. Pat. No. 4,432,966, issued on Feb. 21, 1984, Roussel-UCLAF, teaches a compressed tablet with an active agent, coated with a first coating layer comprising a mixture of microcrystalline cellulose and lower alkyl ether of a cellulose film-forming organic polymer such as ethyl cellulose, and a second coating layer selected from cellulose acetylphthalate, hydroxypropyl methylcellulose phthalate, benzophenyl salicylate, cellulose acetosuccinate, copolymers of styrene and of maleic acid, formylated gelatin, salol, keratin, steraric acid, myristic acid, gluten, acrylic and methacrylic resins, and copolymers of maleic acid and phthalic acid derivatives.

In addition, the art also teaches that certain coating compositions are advantagous for ease of processing. For example, U.S. Pat. No. 5,330,759, issued Jul. 19, 1994, Sterling Winthrop, Inc., teaches soft capsules coated with an enteric coating comprising from about 1 to about 20 mg./cm$^2$ of 1:1 copolymer of methacrylic acid and methyl or ethyl acrylate or methyl or ethyl methacrylate and a plasticizer. Glidants such as talc, to prevent agglomeration of the capsules, and a subcoating, to stiffen the capsules and thereby prevent distortion during coating, are not needed. This reference does not teach colonic delivery nor the importance of a smooth substrate surface without edges or sharp curves, and the coating levels are outside the levels of the present invention.

In addition, dosage forms with higher levels of coating are also known in the art. For example U.S. Pat. No. 5,068,110, issued on Nov. 26, 1991, Warner-Lambert Co., teaches dosage forms with a high level of enteric coating using aqueous systems in their manufacturer, such as Eudragit® L30D, Aquateric® (cellulose acetate phthalate) and Coateric® (polyvinyl acetate phthalate), for improved dissolution stability for storage under high stress conditions. The coating levels disclosed are from 14 mg/cm$^2$ to 24 mg/cm$^2$, which are outside the range of the present invention. These dosage forms are delivered to the small intestine as opposed to the colon.

In summary, colonic delivery of a peroral unit dosage form from which bisacodyl rapidly dissolves in the colon, will provide a higher in-situ concentration of the active compound for a more localized effect, permitting the use of lower doses, resulting in lower side effects. Therefore, a peroral dosage form which will preserve bisacodyl throughout the upper part of the gastrointestinal tract and thereafter rapidly release it in the colon, is desireable.

It is an object of the present invention to provide a dosage form of bisacodyl which provides laxation efficacy to patients without the occurrence of significant side effects such as substantial secondary diarrhea, repeat bowel movements and cramping.

It is a further object of the present invention to provide laxation efficacy at substantially lower doses than is required with current peroral dosage forms of bisacodyl.

SUMMARY OF THE INVENTION

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:
  a. a safe and effective amount of rapidly dissolving bisacodyl incorporated into or coated on the surface of a dosage form selected from the group consisting of a spherical substrate, an elliptical substrate, a hard capsule, or a compressed tablet, with a maximum diameter of about 3 mm to about 10 mm; and
  b. an enteric polymer coating material;
wherein the dosage form has a smooth surface free from edges or sharp curves; the elliptical substrate and the hard capsule have a ratio of the long to short diameters of no greater than about 1.5; the rapidly dissolving bisacodyl is released at a point near the inlet to, or within the colon; the enteric polymer coating material begins to dissolve in an aqueous media at a pH of between about 5 to about 6.3; the enteric polymer coating material has a coating thickness of at least about 250 µm; and wherein the incorporation of the bisacodyl into or on the dosage form is such that bisacodyl dissolves rapidly from the dosage form.

DETAILED DESCRIPTION OF THE INVENTION

It has been surprisingly discovered that laxation in rats (measured as acceleration of transit time through the colon and increase in output of fecal material) produced by delivery of bisacodyl to the colon, is a function of the dissolution rate (dose multiplied by intrinsic dissolution rate) of the administered drug, whereas side effects such as secondary episodes of diarrhea are a function of total administered dose. Thus, bisacodyl administered in the colon as a suspension of very fine, rapidly dissolving particles (essentially all particles less than 10 µm), or in a solubilized form, for example an inclusion complex with hydroxypropyl-β-cylcodextrin, produces maximal laxation in rats at low total doses which do not evoke secondary episodes of diarrhea. In contrast, delivery to the colon of a suspension of more slowly dissolving forms of bisacodyl requires significantly higher doses to produce maximal laxation which also evoke secondary episodes of diarrhea. It has been further demonstrated that there is a linear relationship between cumulative bisacodyl dissolution and acceleration of colonic transit, a measure of laxative efficacy. Therefore, low doses of rapidly dissolving bisacodyl administered in the colon provide laxation efficacy equivalent to larger doses of more slowly dissolving bisacodyl, with reduced side effects.

Although not wishing to be bound by theory, it is believed that the elimination of secondary diarrhea of colonically delivered doses of rapidly dissolving bisacodyl is due to significantly reduced absorption and subsequent biliary recirculation of bisacodyl derived species. Reduced absorption is believed to be the result of colonic delivery (no absorption from the small intestine where the drug is therapeutically inactive), a lower dose, and the laxative effect of the drug which serves to evacuate unabsorbed drug from the colon.

The present invention relates to a pharmaceutical composition in a unit dosage form for peroral administration in a human or lower animal, having a gastrointestinal tract comprising a small intestine and a colon with a lumen therethrough having an inlet to the colon from the small intestine, comprising:
  a. a safe and effective amount of rapidly dissolving bisacodyl incorporated into or coated on the surface of a dosage form selected from the group consisting of a spherical substrate, an elliptical substrate, a hard capsule, or a compressed tablet, with a maximum diameter of about 3 mm to about 10 mm; and
  b. an enteric polymer coating material;
wherein the dosage form has a smooth surface free from edges or sharp curves; the elliptical substrate and the hard capsule have a ratio of the long to short diameters of no greater than about 1.5; the rapidly dissolving bisacodyl is released at a point near the inlet to, or within the colon; the enteric polymer coating material begins to dissolve in an aqueous media at a pH between about 5 to about 6.3; the enteric polymer coating material has a coating thickness of at least about 250 µm; and wherein the incorporation of the bisacodyl into or on the dosage form is such that bisacodyl dissolves rapidly from the dosage form.

Preferably for a spherical substrate, an elliptical substrate, hard capsule or compressed tablet having a diameter of about 3 mm (the long diameter for the elliptical substrate or hard capsule), the minimum coating thickness is about 60 mg./cm$^2$. Preferably for a spherical or elliptical substrate, hard capsule or a compressed tablet having a diameter of about 10 mm (the long diameter for the elliptical substrate or hard capsule), the minimum coating thickness is about 30 mg./cm$^2$.

The dosage forms of the present invention are to be distinguished from controlled (sustained) release compositions which slowly release a drug active over an extended period of time and extend the duration of drug action over that achieved with conventional delivery. The dosage forms of the present invention prevent the release of the drug active until the dosage form reaches the colon.

Rapidly Dissolving Bisacodyl

The methods and compositions of the present invention comprise a safe and effective amount of rapidly dissolving bisacodyl. The phrase "safe and effective amount", as used herein, means an amount of rapidly dissolving bisacodyl high enough to provide a significant positive modification of the condition to be treated, but low enough to avoid serious side effects (at a reasonable benefit/risk ratio), within the scope of sound medical judgment. A safe and effective amount of rapidly dissolving bisacodyl will vary with the particular condition being treated, the age and physical condition of the patient being treated, the severity of the condition, the duration of the treatment, the nature of concurrent therapy and like factors. As indicated hereinabove, an effective dose of rapidly dissolving bisacodyl in compositions of the present invention is preferably substantially lower than the dose of bisacodyl required to achieve efficacy with conventional bisacodyl compositions.

A safe and effective dose of rapidly dissolving bisacodyl in a composition of the present invention preferably provides from about 0.5 mg to about 15 mg of bisacodyl locally, in a unit dosage form, to the lumen of the lower gastrointestinal tract near the inlet of the small intestine to the colon or within the colon of a human patient. A preferred amount of bisacodyl dosed to a human patient is from about 0.75 mg to about 10 mg; more preferred is from about 1 mg to about 5 mg; more preferred still is from about 1 mg to about 3 mg; still more preferred is from about 2 mg to about 3 mg; also preferred is less than about 3 mg; also preferred is less than about 2 mg. The dosage unit form of the present invention preferably contains a single dose of bisacodyl in the above amounts.

As used herein, "rapidly dissolving bisacodyl" is bisacodyl in a physical form or composition which enhances the rate of dissolution of bisacodyl in the intestinal juices in the lumen of the colon compared to conventional bisacodyl formulations. For example the essentially complete dissolution of bisacodyl from the dosage forms of the present invention occurs within about 100 minutes, preferably within about 60 minutes, after substantially complete dissolution of the enteric coating in 0.2M pH 6.5 sodium phosphate buffer, with 0.5% sodium lauryl sulfate at a flow rate of 2 mL/minute in a 12 mm diameter flow through dissolution cell corresponding to USP apparatus 4. As used herein, "conventional bisacodyl formulations" are solid dosage forms of bisacodyl that do not disintegrate when in contact with an aqueous medium. Commercially-available bisacodyl compositions are typically coated with a low level of an enteric polymer or combination of polymers that is insoluble at pH's below about 6.5. An example of such a product is Dulcolax® (Boehringer Ingelheim Pharmaceuticals, Ridgefield, Conn.).

In the compositions of the present invention the rapidly dissolving bisacodyl is selected from the group consisting of micronized bisacodyl, inclusion complex of bisacodyl and a cyclodextrin, solid dispersion of bisacodyl on a hydrophilic substrate, commercially available bisacodyl powder, and any of the preceding solids or solid compositions suspended in a self-emulsifying lipid vehicle, said vehicle being a liquid at 37° C. and a vehicle in which bisacodyl is not soluble.

The micronized bisacodyl, inclusion complex of bisacodyl and a cyclodextrin, solid dispersion of bisacodyl on a hydrophilic substrate, and commercially available bisacodyl powder may be admixed with various other solid pharmaceutically acceptable excipients to enhance the dissolution rate of bisacodyl by promoting disintegration into primary drug particles to maximize surface area. Acceptable excipients include, but are not limited to, diluents (e.g., lactose, sucrose, glucose, starch, calcium sulfate, dicalcium phosphate, micro crystalline cellulose); binders (e.g., polyvinylpyrrolidone, pregelatinized starch, gelatin, hydroxypropyl methylcellulose, methylcellulose, hydroxyethyl cellulose, hydroxypropyl cellulose); lubricants (e.g., stearic acid, magnesium stearate); disintegrants (e.g., sodium starch glycolate, cross-linked polyvinylpyrrolidone, cross-linked carboxymethyl cellulose); glidants (e.g., fumed silica); and buffers. Pharmaceutical excipients are disclosed in "Remington's Pharmaceutical Sciences", 17th Ed. (1985), pp. 1603–1644, which is herein incorporated by reference. The solids mixture may be prepared via a number of techniques well-known in the pharmaceutical sciences such as dry mixing, wet granulation, and fluid bed granulation, and be coated on the surface of, or incorporated into a spherical substrate, elliptical substrate, or incorporated into a hard capsule or compressed tablet, using conventional equipment and processes.

Alternately, the above disclosed solid mixtures may be suspended in a self-emulsifying lipid vehicle, said vehicle being a liquid at 37° C. and one in which bisacodyl is not soluble, which may then be incorporated into a spherical substrate, elliptical substrate or hard capsule. The self-emulsifying lipid vehicle is comprised of a lipophilic liquid in which bisacodyl is not soluble such as medium chain triglycerides, vegetable oils, and parafin oils, and one or more surfactants sufficient to rapidly disperse the lipophilic liquid in an aqueous medium. The surfactants should be miscible with the lipophilic vehicle. The ratio of lipophilic liquid to surfactant is typically about 1:1 to about 5:1, preferably about 2:1 to 3:1. The structures, HLBs, and levels of selected surfactants are dependent upon the lipophilic liquid employed and determined by methods well known to those skilled in the art. As used herein, HLB refers to the hydrophilic/lipophilic balance of the molecule as described in W. C. Griffin, "Classification of Surface-Active Agents by HLB", *Journal of the Society of Cosmetic Chemistry*, Vol. 1, No. 5 (1949), p. 311. The self-emulsifying lipid vehicle containing a suspension of rapidly dissolving bisacodyl may be incorporated into a spherical or elliptical substate or hard capsule, disclosed below, using conventional equipment and processes.

A preferred rapidly dissolving bisacodyl of the present invention comprises micronized bisacodyl, optionally admixed with various solid excipients in order to promote disintegration of the drug from the substrate as primary drug particles to maximize bisacodyl dissolution. As used herein, "micronized bisacodyl", means solid bisacodyl which is finely divided. The particle size distribution of micronized bisacodyl is preferably such that greater than 90% of the particles are less than 10 μm in effective diameter, more preferably greater than 95% are less than 10 μm in effective diameter, more preferably still, greater than 99% are less than 10 μm in effective diameter. As used herein, "effective diameter" means the mean volume diameter, which is equivalent to the diameter of a sphere of equal volume to the particle being measured. Micronized bisacodyl, optionally admixed with various solid excipients, may be incorporated onto the surface of, or into a spherical substrate, an elliptical substrate, or incorporated into a hard capsule or compressed tablet. Micronized bisacodyl, optionally admixed with various solid excipients, may also be suspended into a self-emulsifying lipid vehicle and incorporated into a spherical substrate, an elliptical substrate, or a hard capsule.

Another preferred rapidly dissolving bisacodyl is comprised of an inclusion complex of bisacodyl and a cyclodextrin, optionally admixed with various solid excipients in order to promote disintegration of the inclusion complex from the substrate as primary particles to maximize bisacodyl dissolution. As used herein, "cyclodextrin", means a cyclic carbohydrate molecule comprising six, seven, or eight glucose monomers arranged in a donut shaped ring which are termed $\alpha$-, $\beta$-, and $\gamma$-cyclodextrin, respectively. See J. Pitha, L. Szente & J. Szejtli, "Molecular Encapsulation of Drugs by Cyclodextrins and Congeners", *Controlled Drug Delivery*, Vol. 1, S. D. Brunk, ed., CRC Press, Inc., Boca Raton, Fla., 1983, which is incorporated herein by reference. These molecules may also be modified by the addition of substituents such as hydroxypropyl groups to the hydroxyl groups of the glucose monomers on the outside of the ring. As used herein, "inclusion complex" means a complex between one or more bisacodyl molecules and one or more cyclodextrin molecules in which all or a portion of the bisacodyl molecule or molecules resides in the cavity or cavities of the cyclodextrin molecule or molecules without the formation of a covalent bond between the bisacodyl and cyclodextrin molecules. The molecular ratio of cyclodextrin to bisacodyl preferably ranges from about 0.5:1 to about 30:1 preferably from about 1:1 to about 10:1.Mixtures of cyclodextrins may also be used. Such complexes of cyclodextrin and bisacodyl may be prepared by any of a number of means well known to those skilled in the art, such as solubilization of bisacodyl in an aqueous solution of the cyclodextrin followed by spray drying or lyophilization of the resulting solution to produce a dry powder of the inclusion complex.

Cyclodextrin inclusion complexes of bisacodyl, optionally admixed with various solid excipients, may be incorporated onto the surface of, or into a spherical substrate, an elliptical substrate, or incorporated into a hard capsule or compressed tablet. Cyclodextrin inclusion complexes of bisacodyl, optionally admixed with various solid excipients, may also be suspended into a self-emulsifying lipid vehicle and incorporated into a spherical substrate, an elliptical substrate, or a hard capsule.

Another preferred type of rapidly dissolving bisacodyl consists of a solid dispersion of bisacodyl on a hydrophilic substrate such as fumed silica and others known to one skilled in the art, optionally admixed with various solid excipients in order to promote disintegration of the solid dispersion from the substrate as primary particles to maximize bisacodyl dissolution. Typical ratios (weight:weight) of hydrophilic substrate to bisacodyl range from about 5:1 to about 20:1, preferably from about 8:1 to about 12:1. The solid dispersions may be prepared by mixing a solution of bisacodyl in a pharmaceutically suitable solvent such as acetone with the hydrophilic substrate followed by evaporation of the solvent using any number of processes well known to those skilled in the art.

Solid dispersions of bisacodyl on a hydrophilic substrate, optionally admixed with various solid excipients, may be incorporated onto the surface of, or into a spherical substrate, an elliptical substrate, or incorporated into a hard capsule or a compressed tablet. Solid dispersions of bisacodyl on a hydrophilic substrate, optionally admixed with various solid excipients, may also be suspended into a self-emulsifying lipid vehicle and incorporated into a spherical substrate, an elliptical substrate, or a hard capsule.

A further preferred type of bisacodyl consists of commercially available bisacodyl powder, corresponding to USP specifications, admixed with various solid excipients in order to promote disintegration of the drug from the substrate as primary particles to maximize bisacodyl dissolution. Bisacodyl powder may also be suspended into a self-emulsifying lipid vehicle and incorporated into a spherical substrate, an elliptical substrate, or a hard capsule.

The Dosage Form

A safe and effective amount of rapidly dissolving bisacodyl is incorporated into or coated on the surface of a dosage form selected from the group consisting of a spherical substrate, an elliptical substrate, a hard capsule, or a compressed tablet, with a maximum diameter of about 3 mm to about 10 mm; wherein the dosage form has a smooth surface free from edges or sharp curves; the elliptical substrate and the hard capsule have a ratio of the long to short diameters of no greater than about 1.5.

Preferably the dosage forms of the present invention are selected from the group consisting of a soft gelatin capsule; molded sphere or elipsoid made from any pharmaceutically acceptable excipient that can be melted or molded; a sphere prepared by coating a substrate onto a seed crystal made of any inert pharmaceutically acceptable excipient; hard capsules without edges, having flat seals; and compressed tablets, wherein the dosage form has a smooth surface free from edges or sharp curves, and the elliptical substrate and the hard capsule have a ratio of the long to short diameters of no greater than about 1.5.

As used herein, "elliptical substrate" means an elipsoid, a solid figure in which all plane surfaces are elipses or circles, described by the equation $x^2/a^2+y^2/b^2+z^2/c^2$, wherein b=c, a/b$\leq$1.5, and "a" is between 3 and 10 mm.

As used herein, "smooth surface free from edges or sharp curves" means that no edges exist on the dosage form sufficient to produce thin spots in the enteric coating relative to the mean coating thickness. Especially preferred dosage forms are spheres with a diameter of about 3 mm to about 8 mm; more preferably about 4 mm to about 7 mm. Preferably all of the dosage forms are of a uniform size prior to coating with the polymer coating material. Preferably the diameter of every sphere is within about 5%, more preferably within about 2%, of the mean diameter. The smooth surface and uniform size allow for uniform coating thickness and uniform dissolution of the polymer coating material.

The dosage form preferably consists of an inert spherical substrate prepared by coating and/or layering processes such as sugar spheres, NF. These substrates are sized to obtain the desired uniform diameter by sieving and/or by weighing, i.e. separated by using a weight checker. Preferably the diameter of substantially all of the spheres is within about 5%, more preferably within about 2%, of the mean diameter. They are subsequently coated with rapidly dissolving bisacodyl. The rapidly dissolving bisacodyl is preferrably bound to the sugar sphere substrate with a water soluble, inert polymer, preferably low viscosity hydroxypropyl cellulose or hydroxypropyl methylcellulose. The ratio of the binding polymer to rapidly dissolving bisacodyl is from about 1:10 to 10:1; preferably from about 1:5 to 5:1; more preferably from about 1:4 to 1:1.

The rapidly dissolving bisacodyl on the sugar sphere may be optionally overcoated with an inert, water soluble polymer, to a thickness of about 10 µm to about 50 µm;

preferably about 20 μm to about 40 μm. This overcoat is referred to herein as a barrier coating. The barrier coating preferably consists of low viscosity hydroxypropyl methylcellulose. When the substrate is a sugar sphere and when the enteric polymer coating material is cellulose acetate phthalate, then preferably the dosage form also comprises a barrier coating between the bisacodyl and the cellulose acetate phthalate. The coating of rapidly dissolving bisacodyl and the barrier coating may be applied to the commercially available inert spherical substrate by any number of processes well known to those skilled in the art, including, but not limited to, perforated pan coating and fluid bed coating.

The dosage form may also perferably comprise an inert molded spherical or elliptical substrate. As used herein, "molding" refers to a process in which a molten or semisolid inert, pharmaceutically acceptable material is injected into a mold cavity and allowed to solidify. The dimensions of the mold cavity thereby determine those of the substrate. Suitable materials include, but are not limited to, ingestible pharmaceutically acceptable waxes such as beeswax, paraffins, carnuba wax, and triglycerides with a melting point above about 50° C. such as tristearin. These substrates are coated with rapidly dissolving bisacodyl and optionally overcoated with a water soluble, inert polymer as described above.

A further preferred unit dosage form is a spherical or elliptical soft elastic gelatin capsule. The soft elastic gelatin capsule is filled with rapidly dissolving bisacodyl suspended in a self-emulsifying lipid vehicle as described above.

A still further preferred unit dosage form is a hard capsule (i.e. starch or gelatin hard capsules) without edges, having flat seals where the long to short diameter is no greater than 1.5. An example is a starch capsule free from surfaces edges available under the trade name Capill® from Capsulgel (Greenwood, S.C.) in which the length of the long axis of the capsule is less than about 10 mm and not more than about 1.5 times greater than the short axis diameter of the capsule. The starch capsule may be filled with a solid form of rapidly dissolving bisacodyl as described above, or alternatively with rapidly dissolving bisacodyl dispersed in a self-emulsifying lipid vehicle using conventional processes.

An additional preferred unit dosage form is a compressed spherical or elliptical tablet with a maximum diameter of about 3 to about 10 mm free from surface edges and sharp curves. The tablet is comprised of a solid form of rapidly dissovling bisacodyl and is compressed using conventional equipment and processes. Any compressed tablet preferably is made such that it rapidly disintegrates in intestinal juices.

The Enteric Polymer Coating Material

In the compositions of the present invention, the polymer coating material prevents the release of bisacodyl as the dosage form passes through the upper gastrointestinal tract, including the mouth, esophagus, stomach, and small intestine, until the dosage form is near the junction between the small intestine and the colon or is in the colon. This precludes systemic absorption of bisacodyl and/or desacetyl bisacodyl from the upper gastrointestinal tract (and subsequent biliary excretion of metabolic conjugates), and/or dilution of the released bisacodyl in the contents of the upper gastrointestinal tract (which results in a less concentrated dose of the drug reaching the site of activity in the colon). Therefore, the polymer coating material, in combination with rapidly dissolving bisacodyl and a spherical or elliptical substrate, provides a method of delivering bisacodyl in a concentrated and rapidly dissolving form to the colon. This results in effective laxation at a low dose of the drug with reduced absorption of bisacodyl and/or its metabolites which results in lower side effects such as secondary diarrhea produced by biliary excretion of metabolic conjugates.

As used herein, "enteric polymer coating material", is a material or materials which completely surround and encase the bisacodyl in the unit dosage form prior to oral administration. The polymer coating material of the present invention does not contain any active compound, i.e. bisacodyl, of the present invention. In addition the present invention does not comprise enteric coated microcrystal spheres or particles of the active compound or enteric coated granules of the active compound. Preferably, a substantial amount or all of the enteric polymer coating material is dissolved before the bisacodyl is released from the dosage form, so as to achieve rapid dissolution of the bisacodyl.

The polymer coating material is selected such that rapidly dissolving bisacodyl will be released at about the time that the dosage form reaches the inlet between the small intestine and the colon, or thereafter in the colon. Preferred coating materials include pH-sensitive materials, which remain intact in the lower pH environs of the stomach and small intestine, but which disintegrate or dissolve at the pH commonly found in the latter portion of the small intestine or beginning of the colon or in the colon of the patient. These polymers have a low apparent pKa range to minimize the impact of small intestinal pH variability as well as the drop in the pH across the ileo-cecal valve. The enteric polymer coating material begins to dissolve in an aqueous solution at a pH between about 5 to about 6.3.

The enteric polymer of the present invention is a polyanionic polymer that is insoluble in water and in aqueous solutions with a pH below about 5 to about 6.3. The solubility of the enteric polymer as a function of pH should be such that it is insoluble in the relatively acidic environment of the stomach, but soluble throughout most of the small intestine and colon. It is particularly important that the enteric polymer be soluble in the proximal portions of the colon where the lumenal pH is typically lower than that in the distal portions of the small intestine due to the presence of short chain fatty acids produced by the metabolic activity of bacteria residing in the colon.

The enteric polymer coating material is selected from the group consisting of cellulose acetate phthalate, cellulose acetate trimelliate, hydroxypropyl methylcellulose phthalate, hydroxypropyl methylcellulose acetate succinate, polyvinyl acetate phthalate, poly(methacrylic acid, methyl methacrylate) 1:1, poly(methacrylic acid, ethyl acrylate) 1:1, and compatable mixtures thereof, preferably cellulose acetate phthalate, poly(methacrylic acid, methyl methacrylate) 1:1, and compatable mixtures thereof, more preferably cellulose acetate phthalate. The coating thickness is at least about 250 microns, more preferably at least about 350 microns per unit dosage form. The 250 micron coating thickness is equivalent to about 30 mg./cm$^2$ (for a dosage form with about a 10 mm diameter) to about 60 mg./cm$^2$ (for a dosage form with about a 3 mm diameter.)

Specific examples of suitable polymer coating materials include the following: Eudragit® L, an anionic copolymer derived from methacrylic acid and methyl methacrylate, with a ratio of free carboxyl groups to the ester groups of approximately 1:1, and a mean molecular weight of approximately 135,000;

Eudragit® L 30 D, an aqueous acrylic resin dispersion, an anionic copolymer derived from methacrylic acid and ethyl acrylate with a ratio of free carboxyl groups to the ester groups of approximately 1:1, and a mean molecular weight of approximately 250,000; (it is supplied as an aqueous dispersion containing 30% w/w of dry lacquer substance);

Eudragit® L 100-55, an anionic copolymer derived from methacrylic acid and ethyl acrylate, with a ratio of free carboxyl groups to the ester groups of approximately 1:1, and a mean molecular weight greater than about 100,000;

cellulose acetate phthalate or CAP®, available from Eastman Chemical;

cellulose acetate trimelliate, CAT® available from Eastman Chemical;

hydroxypropyl methylcellulose phthalate (USP/NF type 220824) HPMCP 50® and (USP/NF type 200731) HPMCP 55® available from Shin Etsu Chemical; polyvinyl acetate phthalate, PVAP®, available from Colorcon; hydroxypropyl methylcellulose acetate succinate, HPMCAS®, available from Shin Etsu Chemical.

A preferred polymer coating material is cellulose acetate phthalate (CAP®), wherein for diameters of about 4 to about 7 mm, the preferred coating thickness is about 350 to 1000 µm and about 250 to 800 µm, respectively.

Another preferred polymer is poly(methacrylic acid, methyl methacrylate) 1:1 (Eudragit® L), wherein for diameters of about 4 to about 7 mm, the preferred coating thicknesses is about 400 to about 1200 µm and about 300 to about 1000 µm, respectively.

The amount of enteric polymer coating on the dosage form must be sufficient such that complete dissolution of the coating does not occur until the dosage form is at a location within the gastrointestinal tract near the opening to, or within the colon, thereby releasing bisacodyl in the colon. This necessitates the requirement of a dosage form free from surface edges or sharp curves which will produce thin spots in a coating. The coating over such thin spots will dissolve prior to the dosage form reaching the colon, resulting in premature release of bisacodyl.

Transit of pharmaceutical dosage forms through the gastrointestinal tract has been characterized in the literature (i.e., M. Ashford and J. T. Fell, *J. Drug Targeting*, 1994, Vol. 2, pp. 241–258). Gastric emptying of pharmaceutical dosage forms can be highly variable, but transit through the small intestine is relatively constant with a mean transit time of about three hours. The pH - solubility behavior of the enteric polymers of the present invention is such that significant dissolution of the enteric polymer coating will not occur until the dosage form has emptied from the stomach, thereby eliminating the varibility of gastric emptying as a factor in determining the amount of coating required to achieve release of bisacodyl in the colon. The pH of the small intestine gradually increases from about 5 to 5.5 in the duodenal bulb to about 7.2 in the distal portions of the small intestine (ileum). The pH drops significantly at the ileocecal junction to about 6.3 and very gradually increases to about 7 in the left or descending colon. In order to provide predictable dissolution corresponding to the small intestine transit time of about 3 hours and permit reproducible release of drug at the inlet between the small intestine and the colon, or thereafter in the colon, the coating should begin to dissolve within the pH range of the small intestine and continue to dissolve at the pH of the proximal colon. Therefore, the amount of enteric polymer coating should be such that it is substantially dissolved during the approximate three hour transit time of the small intestine.

Dissolution of enteric polymers of the present invention is influenced by the size of the dosage form, and the pH, ionic strength, and velocity of the surrounding aqueous medium. The latter three factors vary throughout the length of the small intestine and colon. In addition, the effect of these factors upon dissolution rate varies with each enteric polymer. Therefore, an important aspect of the present invention is the amount, or thickness of the enteric polymer coating that is required to delay the release of the drug until the dosage form has reached the colon. Although the requisite amount of enteric polymer will vary as a function of the size of the dosage form and the type of enteric polymer, the minimum amounts as discussed below are well in excess of those known in the art.

The more important parameters for determination of the amount of enteric polymer required to delay drug release until the dosage form has reached the colon have been found to include the pH solubility profile of the enteric polymer and the size of the dosage form. Approximate minimum amounts of enteric polymer as a function of the pH at which the polymer begins to dissolve and dosage form size are shown in the following table, Table 1. Also included are examples of enteric polymers.

TABLE 1

| Diameter (mm) | pH | Amt. Polymer (mg) | Minimum Thickness (µm) | Polymer/ Surf. Area (mg/cm$^2$) | Example Enteric Polymers |
|---|---|---|---|---|---|
| 3 | 5.0 | 23 | 520 | 81 | HPMCP ® 50 |
| 5 | 5.0 | 46 | 437 | 58 | PVAP ® |
| 10 | 5.0 | 127 | 338 | 40 | CAT ® |
| 3 | 5.5 | 22 | 511 | 79 | HPMCP ® 55 |
| 5 | 5.5 | 45 | 430 | 57 | Eudragit ® L100-55 |
| 10 | 5.5 | 125 | 332 | 40 | |
| 3 | 6.0 | 19 | 450 | 67 | Eudragit ® L |
| 5 | 6.0 | 38 | 376 | 49 | |
| 10 | 6.0 | 108 | 290 | 34 | |
| 3 | 6.2 | 16 | 390 | 56 | CAP ® |
| 5 | 6.2 | 33 | 326 | 41 | |
| 10 | 6.2 | 92 | 250 | 29 | |

The enteric pan coating material may be applied to the substrate as a solution in a pharmaceutically acceptable solvent such as ethanol, acetone, isopropanol, ethyl acetate, or mixtures thereof; as an aqueous solution buffered with amminium hydroxide, or as a fine dispersion in water using any number of processes known to one skilled in the art, including but not limited to, perforated pan coating and fluid bed coating.

To enhance the elasticity of the coating materials, preferably the coating material of the present invention also comprises a plasticizer. Appropriate plasticizers include polyethylene glycols, propylene glycols, dibutyl phthalate, diethyl phthalate, tributyl citrate, tributyrin, butyl phthalyl butyl glycolate (Santicizer® B-16, from Monsanto, St. Louis, Mo.), triacetin, castor oil and citric acid esters; preferably the plasitcizer is dibutyl phthalate or triethyl citrate. These plasticizers are present in an amount to facilitate the coating process and to obtain an even coating film with enhanced physical stability. Generally the coating material comprises from about 0% to about 50% of a plasticizer, preferably from about 0% to about 25%, more preferably about 10% to about 20% by weight of the polymer.

For cellulose acetate phthalate, the plasticizer is preferably diethyl phthalate, tributyl citrate, tributyrin, butyl phthalyl butyl glycolate or triacetin.

In addition, to facilitate the coating process, the coating material may also comprise inert solid particulates. Preferred inert solid particulates include talc and titanium dioxide.

The selections of optional plasticizer, optional inert solid particulate, and levels thereof, coating formulation type (solvent, ammoniated aqueous solution, or aqueous dispersion), and process are based upon the specific enteric polymer used and the type of dosage form used according to criteria known to those skilled in the art.

Optional Ingredients

The compositions of the present inventions can optionally include active drug ingredients in addition to bisacodyl. Non-limiting examples of other active drug agents and amounts typically present in such compositions include the following: docusate sodium, calcium or potassium, from about 5 mg to about 500 mg, preferably from about 50 mg to about 250 mg; glycyrrhiza extract comprising from about 5% to about 30%, preferably from about 10% to about 16%, glycyrrhizic acid, from about 2 mg to about 200 mg, preferably from about 20 mg to about 100 mg; aloe, from about 50 mg to about 500 mg, preferably from about 195 mg to about 325 mg; peppermint oil, from about 250 mg to about 4000 mg, preferably from about 500 mg to about 2500 mg; poloxamer 188, from about 10 mg to about 500 mg, preferably from about 100 mg to about 250 mg; ginger, from about 650 mg to about 1300 mg; mineral oil, USP, from about 500 mg to about 40 g; preferably from about 800 mg to about 20 g; castor oil, USP, from about 500 mg to about 60 g; preferably from about 1 g to about 45 g; and magnesium hydroxide, from about 500 mg to about 5 g, preferably from about 1 g to about 2.8 g.

Method of Use

Another aspect of the present invention is methods for providing laxation for humans and lower animals in need thereof by peroral administration of the above-described compositions. Conditions for which such laxation may beneficially be provided include the following: constipation, adjunctive therapy for irritable bowel syndrome, and bowel cleansing prior to diagnostic or surgical procedures.

An advantage of providing bisacodyl to patients using the present compositions is that laxation benefits are generally achieved without the secondary diarrhea commonly associated with conventional bisacodyl compositions. Another advantage is that such laxation benefits are often achieved more quickly than with conventional bisacodyl compositions.

Compositions of the present invention described hereinabove are preferably administered when laxation is needed. One dose is often sufficient to provide the needed laxation, but several dosages can be used sequentially when needed. Such sequential doses are preferably provided to a patient from about 8 hours to about 24 hours apart, up to a maximum of about 4 dosages.

Method of Making

The enteric polymer coating material is generally applied onto the dosage forms as solutions in organic solvents. The solvents commonly employed as vehicles are methylene chloride, ethanol, methanol, isopropyl alcohol, acetone, ethyl acetate and combinations thereof. The choice of the solvent is based primarily on the solubility of the polymer, ease of evaporation, and viscosity of the solution.

Some polymers are also available in aqueous systems. Currently, three aqueous enteric polymer coatings are available for commercial use in the United States. These are Eudragit® L30D (methacrylic acid-ethyl acrylate copolymer marketed by Rohm-Haas GmBH, West Germany); Aquateric® (cellulose acetate phthalate-containing product marketed by FMC Corporation, Philadelphia, Pa.); and Coateric® (a polyvinyl acetate phthalate based product marketed by Colorcon, Inc., West Point, Pa.). Unlike organic solutions, these aqueous-based systems can be prepared at high concentration without encountering high viscosity. Also, these aqueous systems do not have the problems associated with the organic systems such as flammability, toxicity of the residual solvent in the dosage form, etc.

Coating can be achieved by methods known to one skilled in the art such as by using fluidized bed equipment, perforated pans, a regular pharmaceutical pan, compression coating, etc. by continuous or short spray methods, or by drenching.

Methods for coating dosage forms with cellulose acetate phthalate are disclosed in Spitael, J. et al., "Enteric Coating using Cellulose Acetate Phthalate", *Manuf. Chem.*, Vol. 57, Issue 8, Aug. 1986 (p. 35, 37), which is incorporated herein by reference.

The following non-limiting examples provide typical formulations for compositions of the present invention, and typical methods for treating human disorders with such compositions.

EXAMPLE 1

A dosage form of the following formulation is prepared as described below:

| Substrate | | Barrier Coat | | Enteric Coat | |
|---|---|---|---|---|---|
| Component | Wt. (mg) | Component | Wt (mg) | Component | Wt (mg) |
| Sugar Sphere, USP | 50 | HPMC, USP[1] | 5 | CAP ®, NF[2] | 70 |
| Micronized Bisacodyl | 3 | | | Dibutyl Phthalate | 18 |
| HPMC, USP[1] | 1 | | | | |

[1]Hydroxypropyl Methylcellulose, USP. Methocel ® E15LV, Dow Chemical.
[2]Cellulose Acetate Phthalate, NF, CAP ®, Eastman Chemical.

Substrate

Bisacodyl, USP is micronized in a fluid energy mill (Sturtevant 4" SDM) using a grinding pressure of 50 psi to produce a powder with 90% of the particles below 10 μm. It is dispersed in water at a level of 2.7% by weight with 0.9% by weight HPMC as a binding polymer and sprayed onto sugar spheres (6.53–6.63 mm diameter) in a perforated pan coater maintaining an outlet air/bed temperature of about 40° C.

Barrier Coat

HMPC is dissolved in water to produce a 4% by weight solution which is coated on the substrates described above in a perforated pan coater maintaining an outlet air/bed temperature of about 40° C.

Enteric Coat

CAP® and dibutyl phthalate are dissolved in a 1:1 solution of ethanol and acetone such that the total solids content is 12.5% by weight (10% CAP, 2.5% dibutyl phthalate). The resulting solution is coated onto the barrier coated substrates above in a perforated pan coater maintaining an outlet air/bed temperature of about 30° C.

EXAMPLE 2

A dosage form of the following formulation is prepared as described below:

| Substrate | | Enteric Coat | |
|---|---|---|---|
| Component | Wt. (mg) | Component | Wt (mg) |
| Medium Chain Triglyceride [1] | 63 | CAP®, NF[2] | 70 |
| Polyoxyl 35 Castor Oil, NF | 2 | Dibutyl Phthalate | 18 |
| Poloxamer 182 | 19 | | |
| Micronized Bisacodyl | 2 | | |
| Colloidal Silicon Dioxide, NF | 4 | | |
| #3 Spherical Soft Elastic Gelatin Capsule | N/A | | |

[1]Captex® 300, ABITEC Corp.
[2]Cellulose Acetate Phthalate, NF, CAP®, Eastman Chemical.

Substrate

Bisacodyl, USP is micronized in a fluid energy mill (Sturtevant 4" SDM) using a grinding pressure of 50 psi to produce a powder with 90% of the particles below 10 µm. Medium chain triglyceride, polyoxyl 35 castor oil, and poloxamer 182 are blended to produce a solution of a self-emulsifying lipid. Micronized bisacodyl and colloidal silicon dioxide are subsequently dispersed in the self-emulsifying lipid vehicle which is then filled into a #3 soft elastic gelatin capsule at a level of 100 mg using conventional equipment.

Enteric Coat

CAP® and dibutyl phthalate are dissolved in a 1:1 solution of ethanol and acetone such that the total solids content is 12.5% by weight (10% CAP®, 2.5% dibutyl phthalate). The resulting solution is coated onto the filled soft elastic gelatin substrates above in a perforated pan coater maintaining an outlet air/bed temperature of about 30° C.

EXAMPLE 3

A dosage form of the following formulation is prepared as described below:

| Substrate | | Barrier Coat | | Enteric Coat | |
|---|---|---|---|---|---|
| Component | Wt. (mg) | Component | Wt (mg) | Component | Wt (mg) |
| Sugar Sphere, USP | 50 | HPMC®, USP[1] | 5 | Eudragit® L[2] | 50 |
| Bisacodyl, USP | 3 | | | Dibutyl Phthalate | 10 |
| Colloidal Silicon Dioxide, NF | 30 | | | Red Ferric Oxide | 8 |
| HPMC®, USP[1] | 20 | | | Talc, USP | 13 |

[1]Hydroxypropyl Methylcellulose, USP. Methocel® E15LV, Dow Chemical.
[2]Poly(methacrylic acid, methyl methacrylate) 1:1, Eudragit® L, Rohm Tech.

Substrate

Bisacodyl, USP is dissolved in acetone to produce a 5% by weight solution. Colloidal silicon dioxide is suspended in this solution and the solvent allowed to evaporate with agitation. The resulting solid is coated onto sugar spheres (3.9–4.1 mm diameter) using a binding solution of 10% HPMC® in water in a CF Granulator (Vector Corp.).

Barrier Coat

HMPC® is dissolved in water to produce a 4% by weight solution which is coated on the substrates described above in a perforated pan coater maintaining an outlet air/bed temperature of about 40° C.

Enteric Coat

Eudragit® L and dibutyl phthalate are dissolved in a solution of isopropanol, acetone, and water (37:9:1) at levels of 8.0% by weight and 1.6% (total weight percent), respectively. Red ferric oxide and talc are then suspended in the solution at levels of 1.2% by weight and 2.1% by weight, respectively. The resulting mixture is coated onto the barrier coated substrates above in a perforated pan coater maintaining an outlet air/bed temperature of about 30° C.

While particular embodiments of the present invention have been described, it will be obvious to those skilled in the art that various changes and modifications of the present invention can be made without departing from the spirit and scope of the invention. It is intended to cover, in the appended claims, all such modifications that are within the scope of this invention.

What is claimed is:

1. A pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of rapidly dissolving bisacodyl incorporated into or coated on the surface of a dosage form selected from the group consisting of a spherical substrate, an elliptical substrate, a hard capsule, or a compressed tablet, with a maximum diameter of about 3 mm to about 10 mm; and b. an enteric polymer coating material;

wherein the dosage form has a smooth surface free from edges or sharp curves; the elliptical substrate and the hard capsule have a ratio of the long to short diameters of no greater than about 1.5; the rapidly dissolving bisacodyl is released at a point near the inlet to, or within the colon; the enteric polymer coating material begins to dissolve in an aqueous media at a pH between about 5 to about 6.3; and the enteric polymer coating material has a coating thickness of at least about 250 µm.

2. The composition of claim 1 wherein the rapidly dissolving bisacodyl is selected from the group consisting of micronized bisacodyl, an inclusion complex of bisacodyl and a cyclodextrin, a solid dispersion of bisacodyl on a hydrophilic substrate, commercially available bisacodyl powder, and one of the preceding solid forms of bisacodyl suspended in a self-emulsifying lipid vehicle, the vehicle being a liquid at 37° C. and one in which bisacodyl is not soluble.

3. The composition of claim 2 wherein the rapidly dissolving bisacodyl also comprises a pharmaceutically acceptable excipient selected from the group consisting of diluents, binders, lubricants, disintegrants, glidants, buffers, and mixtures thereof, to enhance the dissolution rate of bisacodyl by promoting disintegration into primary drug particles to maximize surface area.

4. The composition of claim 2 wherein the rapidly dissolving bisacodyl is micronized bisacodyl.

5. The compositon of claim 1 wherein the dosage form is selected from the group consisting of a soft elastic gelatin capsule; a molded spherical substrate or elliptical substrate made from any pharmaceutically acceptable excipient that can be melted or molded; and a spherical substrate or elliptical substrate prepared by coating or layering a substrate onto a seed crystal made of any inert pharmaceutically acceptable excipient.

6. The composition of claim 5 wherein the dosage form is a soft elastic gelatin capsule or a sugar sphere.

7. The composition of claim 1 wherein the enteric polymer coating material is selected from the group consisting of cellulose acetate phthalate, cellulose acetate trimelliate, hydroxypropyl methylcellulose phthalate, hydroxypropyl methylcellulose acetate succinate, polyvinyl acetate phthalate, poly(methacrylic acid, methyl methacrylate) 1:1, poly(methacrylic acid, ethyl acrylate) 1:1, and compatable mixtures thereof.

8. The composition of claim 7 wherein the enteric polymer coating material is cellulose acetate phthalate.

9. The composition of claim 8 wherein the enteric polymer coating material is plasticized.

10. A pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of micronized bisacodyl incorporated into a soft elastic gelatin capsule with a maximum diameter of about 3 mm to about 10 mm;

b. cellulose acetate phthalate enteric polymer coating material;

wherein the soft elastic gelatin capsule has a smooth surface free from edges or sharp curves; the micronized bisacodyl is released to a point near the inlet to, or within the colon; and the cellulose acetate phthalate has a coating thickness of at least about 250 µm.

11. The composition of claim 10 wherein the cellulose acetate phthalate is plasticized.

12. The composition of claim 10 wherein the micronized bisacodyl has a particle size distribution such that greater than 90% of the particles are less than 10 µm in effective diameter.

13. The composition of claim 12 wherein the micronized bisacodyl has a particle size distribution such that greater than 95% of the particles are less than 10 µm in effective diameter.

14. The composition of claim 13 wherein the micronized bisacodyl is dispersed into a self-emulsifying lipid vehicle, the vehicle being a liquid at 37° C. and one in which bisacodyl is not soluble.

15. The composition of claim 10 wherein the diameter of the soft elastic gelatin capsule is from about 4 mm to about 7 mm.

16. The composition of claim 15 wherein the cellulose acetate phthalate has a coating thickness of about 350 µm to about 1000 µm when the diameter is about 4 mm.

17. The composition of claim 15 wherein the cellulose acetate phthalate has a coating thickness of about 250 µm to about 800 µm when the diameter is about 7 mm.

18. A pharmaceutical composition in a unit dosage form for peroral administration in a human or lower animal, having a gastrointestinal tract comprising a small intestine and a colon with a lumen therethrough having an inlet to the colon from the small intestine, comprising:

a. a safe and effective amount of micronized bisacodyl coated on the surface of a sugar spherical substrate with a maximum diameter of about 3 mm to about 10 mm;

b. cellulose acetate phthalate enteric polymer coating material; and c. a barrier coating which coats the sugar spherical substrate prior to coating with cellulose acetate phthalate enteric polymer coating material;

wherein the sugar spherical substrate has a smooth surface free from edges or sharp curves; the micronized bisacodyl is released to a point near the inlet to, or within the colon; and the cellulose acetate phthalate has a coating thickness of at least about 250 µm.

19. The composition of claim 18 wherein the cellulose acetate phthalate is plasticized.

20. The composition of claim 18 wherein the micronized bisacodyl has a particle size distribution such that greater than 90% of the particles are less than 10 µm in effective diameter.

21. The composition of claim 18 wherein the micronized bisacodyl has a particle size distribution such that greater than 95% of the particles are less than 10 µm in effective diameter.

22. The composition of claim 18 wherein substantially all of the sugar spherical substrates have a diameter within about 5% of the mean diameter.

23. The composition of claim 22 wherein the diameter of the sugar spherical substrate is from about 4 mm to about 7 mm.

24. The composition of claim 23 wherein the cellulose acetate phthalate has a coating thickness of about 350 µm to about 1000 µm when the diameter is about 4 mm.

25. The composition of claim 23 wherein the cellulose acetate phthalate has a coating thickness of about 250 µm to about 800 µm when the diameter is about 7 mm.

26. The composition of claim 18 wherein the barrier coating is hydroxypropyl methylcellulose.

27. A method for providing laxation in the colon of a human or lower animal by administering a safe and effective amount of the composition of claim 1 perorally.

28. A method for providing laxation in the colon of a human or lower animal by administering a safe and effective amount of the composition of claim 10 perorally.

29. A method for providing laxation in the colon of a human or lower animal by administering a safe and effective amount of the composition of claim 18 perorally.

* * * * *